United States Patent [19]

Endo et al.

[11] Patent Number: 5,278,328

[45] Date of Patent: Jan. 11, 1994

[54] PROCESS FOR PRODUCING CARBOXYLIC ACID CHLORIDE

[75] Inventors: Takeshi Endo; Toshikazu Takata; Shinichi Ohno, all of Kanagawa; Fujio Takahashi, Hyogo, all of Japan

[73] Assignee: Nippon Oil & Fats Co., Ltd., Tokyo, Japan

[21] Appl. No.: 849,188

[22] Filed: Mar. 11, 1992

[30] Foreign Application Priority Data

Mar. 12, 1991 [JP] Japan .................................. 3-70320

[51] Int. Cl.$^5$ ............................................. C07C 51/00
[52] U.S. Cl. ..................................... 554/150; 554/151; 554/154; 562/856; 562/857; 562/847; 521/32
[58] Field of Search ............ 554/151, 150, 154; 562/847, 857, 864; 521/32

[56] References Cited

U.S. PATENT DOCUMENTS 2,848,491 8/1958 Mackenzie .......................... 562/854

Primary Examiner—José G. Dees
Attorney, Agent, or Firm—Sughrue, Mion, Zinn, Macpeak & Seas

[57] ABSTRACT

Disclosed is a process for producing a carboxylic acid chloride by reacting phosgene with a carboxylic acid or an anhydride thereof, which comprises effecting the reaction in the presence of a homopolymer or copolymer of a monomer represented by formula (I) or (II) below, a copolymer of the monomers represented by formulae (I) and (II) below, or a copolymer of at least one monomer selected from the group sensisting of the monomers represented by formulae (I) and (II) below with another monomer copolymerizable therewith:

$$CH_2=CHNR^1COR^2 \qquad (I)$$

$$CH_2=CR^3CONR^4R^5 \qquad (II).$$

In these formulae $R^1$, $R^2$, and $R^4$ each represents an alkyl group containing from 1 to 3 carbon atoms, or an alkylene group containing from 3 to 5 carbon atoms provided that $R^1$ with $R^2$, and $R^4$ with $R^5$ may each combine to form a ring structure through $>N-CO-$ or $>N-$ in the molecule; $R^3$ and $R^5$ each represents a hydrogen atom or an alkyl group containing from 1 to 3 carbon atoms; and the alkyl groups and alkylene groups may have substituents which are inactive under the polymerization and chlorination reaction conditions.

3 Claims, No Drawings

PROCESS FOR PRODUCING CARBOXYLIC ACID CHLORIDE

FIELD OF THE INVENTION

The present invention relates to a process for producing a carboxylic acid chloride by reacting phosgene with a carboxylic acid or an anhydride thereof, particularly in the presence of a polymer as a catalyst.

BACKGROUND OF THE INVENTION

Many chlorination processes for producing carboxylic acid chlorides by reacting various types of halogenating agents with carboxylic acids or anhydrides thereof have been heretofore proposed. For example, there are (A) a process using phosphorus pentachloride, as disclosed in J. Am. Chem. Soc., 67 (1954) p. 2239; (B) a process in which phosphorus trichloride is used, as disclosed in J. Chem. Soc., (1954) p. 2030; (C) a process in which phosphorus oxychloride is used, as disclosed in J. Jpn. Oil Chem. Soc. (Yukagaku), 10 (7) (1961) p.435; (D) a process using thionyl chloride, as disclosed in J. Chem. Soc., (1953) p.2117; and (E) a process in which phosgene is used, as disclosed in J. Chem. Soc., 31 (1954) p.151.

The use of phosgene is advantageous in producing high purity carboxylic acid chloride, because the gaseous by-products can be readily removed from the reaction system. Generally, however, the rate of reaction between phosgene and a carboxylic acid or an anhydride thereof is considerably low as compared with that of a reaction which involves a halogenated phosphorus compound. Accordingly, the use of a catalyst is indispensable to accelerate the reaction for producing carboxylic acid chloride in an industrially feasible process using phosgene. In this case, however, as described in detail in JP-A-2-6412 (the term "JP-A-" as referred to herein signifies a "unexamined published Japanese patent application"), the process suffers precipitation of solids and contamination of crude products due to the occurrence of strongly colored decomposed products from the catalysts.

SUMMARY OF THE INVENTION

An object of the present invention is to provide a process for producing carboxylic acid chloride by reacting phosgene with a carboxylic acid or an anhydride thereof using a polymer as a catalyst, said process being such free from forming precipitates and from contaminating the desired reaction product, i.e., carboxylic acid chloride, by strongly colored decomposed catalysts. The product further facilitates recovery and reuse of the catalysts used therein.

Accordingly, the present invention provides a process for producing carboxylic acid chloride by reacting phosgene with a carboxylic acid or an anhydride thereof, which is characterized in that the reaction is effected in the presence of a homopolymer or copolymer of a monomer represented by the formula (I) or (II) below, a copolymer of the monomers represented by formulae (I) and (II) below, or a copolymer of at least one monomer selected from the group consisting of the monomers represented by formulae (I) and (II) below with another monomer copolymerizable therewith:

wherein, $R^1$, $R^2$, and $R^4$ each represents an alkyl group containing from 1 to 3 carbon atoms, or an alkylene group containing from 3 to 5 carbon atoms provided that $R^1$ is combined with $R^2$ and $R^4$ is combined with $R^5$ to form each a ring structure through $>N-CO-$ or $>N-$ in the molecule; $R^3$ and $R^5$ each represents a hydrogen atom or an alkyl group containing from 1 to 3 carbon atoms; and said alkyl groups and alkylene groups may have substituents which are inactive under the polymerization and chlorination reaction conditions.

DETAILED DESCRIPTION OF THE INVENTION

In formulae (I) and (II) which represent the monomers which constitute the polymer for use as a catalyst in the present invention, the alkyl groups containing 1 to 3 carbon atoms represented by $R^1$, $R^2$, $R^3$, $R^4$, and $R^5$ include a methyl, an ethyl, a propyl, and an isopropyl group. The alkyl groups may have substituents which are inactive under the conditions for polymerization and chlorination reactions, such as a halogen atom, an alkoxy group (e.g., methoxy and ethoxy), an alkoxycarbonyl group (e.g., methoxycarbonyl and ethoxycarbonyl), and a phenyl group. The alkylene groups which form ring structures through combinations of $R^1$ with $R^2$, and $R^4$ with $R^5$ may further have substitutes such as an alkyl group (e.g., methyl and ethyl), a halogen atom, an alkoxyl group, an alkoxycarbonyl group, and a phenyl group. The rings formed through these combinations include a pyrrolidone ring, a piperidone ring, a pyrrolidine ring, a piperidine ring, and a hexamethyleneimine ring. As specific compounds represented by formulae (I) and (II) above, there are mentioned, for example, N-vinyl-2-pyrrolidone, N,N-dimethylacrylamide, N,N-dimethylmethacrylamide, N-methyl-N-vinylacetamide, N-isopropylacrylamide, and N-isopropylmethacrylamide.

The polymer for use as a catalyst in the present invention includes, in addition to the homopolymers and copolymers of the compounds represented by formulae (I) and (II), the copolymers of these compounds and monomers copolymerizable therewith, such as styrene, acrylonitrile, methyl acrylate, methyl methacrylate, ethyl methacrylate, and divinylbenzene. Preferred among them are the copolymers from the point of view that they do not dissolve into the chlorination reaction system, and most preferred are the crosslinked copolymers. The polymer for use as the catalyst in the present invention preferably contains the monomers represented by formula (I) or (II) and other monomers copolymerizable therewith at a molar ratio in the range of, preferably, from 99.9:0.1 to 20:80, more preferably, from 99.9:0.1 to 50:50, and most preferably, from 99.9:0.1 to 70:30. The polymer preferably has a number average molecular weight of 10,000 or higher, more preferably of 50,000 or higher, and most preferably, of 100,000 or higher.

The polymers for use in the present invention can be synthesized by processes as follows: Polymerizing the monomers in a solvent under an inert gas atmosphere using a radical polymerizing catalyst, and then carrying out solvent purification. In the case of a cross-linked polymer, the polymer once subjected to polymerization reaction in the same manner above is crushed and washed with the solvent.

The carboxylic acid chloride is produced by the present invention using the corresponding carboxylic acid or an anhydride thereof as the starting material. More specifically, starting materials for use in the present invention include saturated aliphatic carboxylic acids such as pivalic acid, caproic acid, enanthic acid, caprylic acid, 2-ethylhexanoic acid, pelargonic acid, 2,2-dimethyloctanoic acid, capric acid, lauric acid, myristic acid, palmitic acid, stearic acid, and behenic acid; unsaturated aliphatic carboxylic acids such as oleic acid, linoleic acid, linolenic acid, and erucic acid; aromatic carboxylic acids such as benzoic acid, phenylacetic acid, phenylpropionic acid, and cinnamic acid; dicarboxylic acids such as succinic acid, adipic acid, phthalic acid, isophthalic acid, terephthalic acid, and dimer acid; and anhydrides thereof.

In the process according to the present invention phosgene is added to a carboxylic acid or an acid anhydride thereof at a stoichiometric amount or more with respect to the acyl group thereof, preferably at an amount of from 1.1 to 2.5 equivalents, more preferably of from 1.1 to 2 equivalents, and most preferably, of from 1.1 to 1.5 equivalents, to 1 equivalent of the acyl group.

The homopolymers or the copolymers (referred to collectively as "polymers", hereinafter) which function as the catalyst in the process of the present invention are used in an amount of from 0.01 to 20% equivalent, more preferably, from 0.05 to 10% equivalent, and more preferably, from 0.1 to 5% equivalent in terms of the >N—CO— unit of the polymers with respect to the acyl group in the carboxylic acid or anhydride thereof. The reaction is effected either continuously or discontinuously in the temperature range of from 20° to 150° C., preferably of from 20° to 120° C., and more preferably, of from 30° to 100° C.

The process according to the present invention can be conducted in the presence of an inactive solvent, for example, in an aliphatic or aromatic hydrocarbon such as hexane, cyclohexane, benzene, toluene, and xylene, and an aliphatic or aromatic halogenated hydrocarbon such as methylene chloride, chloroform, carbon tetrachloride, trichloroethane, tetrachloroethane, chlorobenzene, and dichlorobenzene. When a carboxylic acid which is a reactant, or a carboxylic acid chloride, which is a reaction product, functions as a solvent, the reaction may be carried out without using any solvent.

The process according to the present invention comprises charging a carboxylic acid, an inactive solvent, and a polymer for use as the catalyst in a pertinent reactor equipped with a stirrer, and then heating the resulting mixture to the reaction temperature. Phosgene is introduced together with an inert gas into the reaction system after the system reaches the reaction temperature to effect the reaction. The inactive solvent is distilled away upon completion of the reaction, and thus carboxylic acid chloride is obtained by filtering off the catalyst or by distillation.

The polymers used in the present invention as the catalysts are different from the well-known N-alkylcarboxylic acid amide catalysts such as N,N-dimethylformamide and N-methyl-2-pyrrolidone, in that the present catalysts form no or substantially few solid precipitates and that they cause no or little contamination ascribed to the strongly colored decomposed catalysts. Furthermore, since the catalysts for use in the present invention greatly differ in molecular weight from the carboxylic acid chloride, the reaction product, they can be readily separated from the reaction products by distillation or filtration, and then subjected to reuse.

The process according to the present invention efficiently removes the remaining polymers used as the catalysts, easily from the carboxylic acid chloride upon completion of the reaction, and thereby provides at an increased yield, a high-purity carboxylic acid chloride having high quality and a favorable color.

The present invention is described in further detail referring to examples below, but it should be understood that the present invention is not limited thereto. In the following examples, all parts and percentages are by weight unless otherwise indicated.

The reaction was conducted according to the present invention, using the polymers and copolymers listed in Table 1 as the catalyst.

EXAMPLES 1 TO 6

To 50 ml of methylene chloride having dissolved therein 2 g (10 mmole) of lauric acid was added 0.6 ml of tridecane and the catalyst at an amount 4% equivalent to lauric acid, and the resulting mixture was stirred in an argon atmosphere. After the reaction system achieved a stable temperature of 35° C. in an incubator, 1.5 g (15 mmole) of phosgene was introduced therein together with a dry nitrogen gas supplied at a flow rate of 50 ml per minute over an hour. Then, 1 ml of the reaction solution was taken out from the reaction system, which was then added to a mixed solution containing 200 μl of methanol, 168 μl of triethylamine, and 30 μl of trifluoroacetic acid. The methyl laurate thus produced was determined quantitatively by gas chromatography, from the ratio of the detected methyl laurate to an internal standard, tridecane. The results are given in Table 2.

EXAMPLE 7

A similar reaction process as that conducted in Example 1 was carried out using the same starting materials but each at an amount 5 times that used in Example 1, and using the catalyst used in Example 6, i.e., a cross-linked copolymer of N-vinyl-2-pyrrolidone and divinylbenzene. In this Example, the catalyst was composed of particles retained between 100- and 200-mesh sieves. Upon completion of the reaction, the reacted solution was filtered using a glass filter (G-3), and the catalyst residue thus recovered was washed with methylene chloride and dried in vacuum. The solvent thus recovered at an yield of 91% was sieved to obtain particles retained between 100- and 300-mesh sieves, to reuse it as a catalyst in a reaction conducted in way a similar to that in Example 1. The results are given in Table 2.

EXAMPLES 8 TO 16

Into a 500-ml volume four-neck flask equipped with a stirrer, a thermometer, a gas inlet tube, and a condenser was charged each of the carboxylic acids or anhydrides thereof each in a predetermined amount shown in Table 2. To the starting materials thus charged into the flask was added a catalyst in an amount 0.7% equivalent to the starting material, and the system was heated to 70° C. on an oil bath. Then, while stirring, 1.2 equivalents of phosgene to 1 equivalent of the acyl group of the starting material was introduced into the system over 4 hours. Upon completion of the reaction, 5 g of the resulting solution was taken out, and the chlorine content thereof was measured according to A.O.C.S. Official Method Da 9-48. The product (carboxylic acid chloride) yield was determined by comparing each of the results with the calculated value. The results are given in Table 2.

COMPARATIVE EXAMPLES 1 TO 2

The same process of Example 1 was conducted in Comparative Examples 1 and 2, except for using N-methyl-2-pyrrolidone and N,N-dimethylacetamide, respectively, as known catalysts. The results are given in Table 2.

COMPARATIVE EXAMPLES 3 TO 4

The same process of Example 8 was conducted in Comparative Examples 3 and 4, except for using N-methyl-2-pyrrolidone and N,N-dimethylacetamide, respectively, as known catalysts. The results are given in Table 2.

From the results given in Table 2, it can be seen that the processes using the polymers according to the present invention as the catalysts provide at a high yield, a high quality carboxylic acid chloride completely free of or with considerably weak coloration. It is further proved by Example 7 that the catalysts according to the present invention can be recovered and subjected to reuse.

While the invention has been described in detail and with reference to specific embodiments thereof, it will be apparent to one skilled in the art that various changes and modifications can be made therein without departing from the spirit and scope thereof.

TABLE 1

| Catalyst | Monomer Composition of the Polymer[1] | | | Molecular Weight[2] | |
|---|---|---|---|---|---|
| | Monomer (1) | Monomer (2) | Molar ratio(1/2) | Mn | Mw/Mn |
| 1 | N-Vinyl-2-pyrrolidone | — | 100/0 | 315,000 | 3.66 |
| 2 | N-Vinyl-2-pyrrolidone | — | 100/0 | 15,000 | 3.12 |
| 3 | N-Methyl-N-vinylacetamide | — | 100/0 | 214,000 | 1.91 |
| 4 | N,N-Dimethylacrylamide | — | 100/0 | 268,000 | 6.23 |
| 5 | N,N-Dimethylacrylamide | — | 100/0 | 66,000 | 6.19 |
| 6 | N,N-Dimethylmethacrylamide | — | 100/0 | 71,000 | 6.50 |
| 7 | N-Vinyl-2-pyrrolidone | Styrene | 74/26 | 26,700 | 1.65 |
| 8 | N,N-Dimethylacrylamide | Styrene | 70/30 | 356,000 | 1.60 |
| 9 | N,N-Dimethylacrylamide | Styrene | 80/20 | 34,000 | 1.82 |
| 10 | N,N-Dimethylmetacrylamide | Styrene | 40/60 | 38,500 | 1.74 |
| 11 | N-Isopropylacrylamide | Styrene | 80/20 | 11,000 | 2.27 |
| 12 | N-Vinyl-2-pyrrolidone | Divinylbenzene | 75/25 | — | — |
| 13 | N,N-Dimethylacrylamide | Divinylbenzene | 50/50 | — | — |
| 14 | N,N-Dimethylmethacrylamide | Divinylbenzene | 75/25 | — | — |

Note:
[1] The molar ratio of the monomers (1/2) was determined by elemental analysis of the corresponding polymer.
[2] Determined by Gel Permeation Chromatography; Mn: number average molecular weight; Mw: weight average molecular weight.

TABLE 2

| No. | Catalyst | Carboxylic Aciid or Carboxylic Anhydride | | | | | Carboxylic Acid Chloride | | |
|---|---|---|---|---|---|---|---|---|---|
| | | Pivalic acid (g) | 2-Ethylhexanoic acid (g) | Lauric acid (g) | Stearic acid (g) | Benzoic anhydride (g) | Yield (%) | Color (Appearance) | Color[1] (Gardner) |
| Example | | | | | | | | | |
| 1 | 1 | — | — | 2 | — | — | 99 | colorless transparent | — |
| 2 | 3 | — | — | 2 | — | — | 98 | colorless transparent | — |
| 3 | 4 | — | — | 2 | — | — | 99 | colorless transparent | — |
| 4 | 7 | — | — | 2 | — | — | 100 | colorless transparent | — |
| 5 | 8 | — | — | 2 | — | — | 99 | colorless transparent | — |
| 6 | 12 | — | — | 2 | — | — | 100 | colorless transparent | — |
| 7 | 12 (recovered) | — | — | 2 | — | — | 100 | colorless transparent | — |
| 8 | 2 | 200 | — | — | — | — | 100 | — | 2 |
| 9 | 5 | — | 200 | — | — | — | 99 | — | 2 |
| 10 | 6 | — | — | — | 220 | — | 99 | — | 2 |
| 11 | 9 | — | — | 220 | — | — | 100 | — | 1 |
| 12 | 10 | 200 | — | — | — | — | 99 | — | 2 |
| 13 | 11 | — | 200 | — | — | — | 100 | — | 4 |
| 14 | 12 | — | — | — | 220 | — | 100 | — | 1 |
| 15 | 13 | — | — | — | — | 220 | 99 | — | 1 |
| 16 | 14 | — | — | 220 | — | — | 100 | — | 1 |
| Comparative Example | | | | | | | | | |
| 1 | N-methyl-2-pyrrolidone | — | — | 2 | — | — | 100 | yellow transparent | — |
| 2 | N,N-dimethyl-acetamide | — | — | 2 | — | — | 100 | yellow transparent | — |
| 3 | N-methyl-2-pyrrolidone | — | — | 220 | — | — | 100 | — | 14 |
| 4 | N,N-dimethyl- | — | — | — | 220 | — | 99 | — | 12 |

TABLE 2-continued

| | | Carboxylic Acid or Carboxylic Anhydride | | | | | Carboxylic Acid Chloride | | |
|---|---|---|---|---|---|---|---|---|---|
| No. | Catalyst | Pivalic acid (g) | 2-Ethylhexanoic acid (g) | Lauric acid (g) | Stearic acid (g) | Benzoic anhydride (g) | Yield (%) | Color (Appearance) | Color[1] (Gardner) |
| | acetamide | | | | | | | | |

Note:
[1] Gardner: A.O.C.S. Official Method Td 1a-64

What is claimed is:

1. A process for producing carboxylic acid chloride by reacting phosgene with a carboxylic acid or an anhydride thereof, which comprises effecting the reaction in the presence of a homopolymer or copolymer of a monomer represented by formula (I) or (II) below, a copolymer of the monomers represented by formulae (I) and (II) below, or a copolymer of at least one monomer selected from the group consisting of the monomers represented by formulae (I) and (II) below with another monomer copolymerizable therewith:

$$CH_2=CHNR^1COR^2 \quad (I)$$

$$CH_2=CR^3CONR^4R^5 \quad (II)$$

wherein, $R^1$, $R^2$, and $R^4$ each represents an alkyl group containing from 1 to 3 carbon atoms, or an alkylene group containing from 3 to 5 carbon atoms provided that $R^1$ is combined with $R^2$ and $R^4$ is combined with $R^5$ to form each a ring structure through $>N-CO-$ or $>N-$ in the molecule; $R^3$ and $R^5$ each represents a hydrogen atom or an alkyl group containing from 1 to 3 carbon atoms; and said alkyl groups and alkylene groups may have substituents which are inactive under the polymerization and chlorination reaction conditions.

2. The process for producing carboxylic acid chloride as claimed in claim 1, wherein the monomer represented by formula (I) or (II) is at least one compound selected from the group consisting of N-vinyl-2-pyrrolidone, N,N-dimethylacrylamide, N,N-dimethylmethacrylamide, N-methyl-N-vinylacetamide, N-isopropylacrylamide, and N-isopropylmethacrylamide.

3. The process for producing carboxylic acid chloride as claimed in claim 1, wherein the monomer copolymerizable with the monomer of formula (I) or (II) is at least one compound selected from the group consisting of styrene, acrylonitrile, methyl acrylate, methyl methacrylate, ethyl methacrylate, and divinylbenzene.

* * * * *